(12) United States Patent
Fine et al.

(10) Patent No.: US 8,129,329 B2
(45) Date of Patent: Mar. 6, 2012

(54) NATURAL POLYPEPTIDES FOR ORAL HEALTH CARE

(75) Inventors: Daniel Fine, New York, NY (US); Narayanan Ramasubbu, East Windsor, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 410 days.

(21) Appl. No.: 12/523,502

(22) PCT Filed: Jan. 16, 2008

(86) PCT No.: PCT/US2008/051165
§ 371 (c)(1),
(2), (4) Date: Jul. 16, 2009

(87) PCT Pub. No.: WO2008/089234
PCT Pub. Date: Jul. 24, 2008

(65) Prior Publication Data
US 2010/0144598 A1    Jun. 10, 2010

Related U.S. Application Data

(60) Provisional application No. 60/880,753, filed on Jan. 16, 2007.

(51) Int. Cl.
*C07K 14/00* (2006.01)
(52) U.S. Cl. .......................... 514/1; 530/350
(58) Field of Classification Search ....... 514/1; 530/350
See application file for complete search history.

(56) References Cited

U.S. PATENT DOCUMENTS

| | | | |
|---|---|---|---|
| 5,851,788 | A | 12/1998 | Fukuda et al. |
| 6,159,447 | A | 12/2000 | Budny et al. |
| 2004/0136926 | A1 | 7/2004 | Periathamby et al. |

FOREIGN PATENT DOCUMENTS
WO    WO 00/01730    1/2000

OTHER PUBLICATIONS

Zheng Liu et al, Gene expression profiles in human nasal polyp tissues studied by means of DNA microarray, J. Allergy Clin. Immunol. 114(4):783-90 (Oct. 2004).
R.J. Gibbons and D.J. Hay, Adsorbed Salivary Acidic Proline-rich Proteins Contribute to the Adhesion of *Streptococcus mutans* JBP to Apatitic Surfaces, J. Dent. Res. 68(9): 1303-07 (Sep. 1989).
A. Shimotoyodome et al, Statherin and Histatin 1 Reduce Parotid Saliva-Promoted *Streptococcus mutans* Strain MT8148 Adhesion to Hydroxyapatite Surfaces, Caries Research 40:403-11 (2006).
Joseph Sambrook et al, Molecular Cloning: A Laboratory Manual 10.1-10.52 (3d ed. 2001).
International Search Report for PCT/US08/51165 dated Oct. 3, 2008.
Supplemental European Search Report for EP08705953.1 (Aug. 24, 2010).
Gilbert, Michele et al., "Chimeric Peptides of Statherin and Osteopontin That Bind Hydroxyapatite and Mediate Cell Adhesion," The Journal of Biological Chemistry, vol. 275, No. 21, pp. 16213-16218 (May 26, 2000).
Sreenivasan, P.K., "Antimicromial Effects of A New Therapeutic Liquid Dentifrice Formulation On Oral Bacteria Including Odorigenic Species," Clinical Oral Investigations, vol. 9, No. 1, pp. 38-45 (Mar. 1, 2005).
Velliyagounder, Kabilan et al., "One of Two Human Lactoferrin Variants Exhibits Increased Antibacterial and Transcriptional Activation Activities and Is Associated with Localized Juvenile Periodontitis," Infection and Immunity, vol. 71, No. 11, pp. 6141-6147 (Nov. 2003).
Communication pursuant to Article 94(3) EPC for EP08705953.1 (May 11, 2011).

*Primary Examiner* — Karen Carlson
(74) *Attorney, Agent, or Firm* — Lowenstein Sandler PC (57) ABSTRACT

The present invention relates generally to dental diseases, caries and periodontal disease. More specifically, the invention relates to Lactoferrin and Statherin fusion proteins (STAT-LF) along with therapeutic, diagnostic and research uses for these polypeptides. The present invention also provides methods of treating dental diseases, caries and periodontal disease.

18 Claims, 5 Drawing Sheets

Figure 1: Peptides for Active Lf fusion peptide a) Lactoferrin (Lf) peptide with the = LF 11
   Amino Acid sequences 21-31

Active Form - FQWQRNMRKVR (SEQ ID NO. 1)
   DNA Dequence – TTCCAATGGCAAAGGAATATGAGAAAAGTGCGT (SEQ ID NO. 2)

Inactive Form: FQWQRNMRRVR (SEQ ID NO. 3)

b) This is the statherin (STAT) peptide = STAT 6
   Amino Acid Sequence:
   DDDEEK (SEQ ID NO. 4)

DNA Sequence:
   GATGATGATGAAGAGAAA (SEQ ID NO. 5)
   GATGATGATGAAGAAAAA (SEQ ID NO. 6)

c) This is the second statherin peptide = STAT 15
   Amino Acid Sequence:
   DDDEEKFLRRIGRFG (SEQ ID NO. 7)

DNA Sequence:
   GATGATGATGAAGAGAAATTTTGCGTAGAATTGGAAGATTCGGT (SEQ ID NO. 8)

d) This is the combined peptide of STAT and LF = STAT- LF 6
   Amino Acid Sequence:
   DDDEEKFQWQRNMRKVR (SEQ ID NO. 9)

STAT-LF 6(a): DNA Sequence

GATGATGATGAAGAGAAATTCCAATGGCAAAGGAATATGAGAAAAGTGCGT (SEQ ID NO.10)

STAT-LF 6(b): DNA Sequence

GATGATGATGAAGAAAAATTCCAATGGCAAAGGAATATGAGAAAAGTGCGT (SEQ ID NO.11)

e) This is the second STAT-LF combined peptide STAT- LF 15
   Amino Acid Sequence:
   DDDEEKFLRRIGRFGFQWQRNMRKVR (SEQ ID NO. 12)

DNA Sequence:
   GATGATGATGAAGAGAAATTTTGCGTAGAATTGGAAGATTCGGT (SEQ ID NO. 13)

FIGURE 2

Figure 3: Left panel = PBS, Middle panel = Arginine; Right panel = Lysine Note zone of inhibition in LF "K" = lysine variant.

Upper left panel= Lf, Middle = Statherin 5 mer, Upper Right = Statherin 15mer
Lower left = Fusion STAT-LF , Lower Right STAT-LF (stat 15mer)
Note that the LF is active as is the STAT-LF with stat as 6mer and with stat as as 15 mer there is less activity.

FIGURE 5

SEQUENCE LISTING

```
<160> NUMBER OF SEQ ID NOS: 13

<210> SEQ ID NO 1
<211> LENGTH: 11
<212> TYPE: PRT
<213> ORGANISM: Artificial Sequence
<220> FEATURE:
<223> OTHER INFORMATION: Active form of synthetic peptide LF11 based on
      human lactoferrin peptide

<400> SEQUENCE: 1

Phe Gln Trp Gln Arg Asn Met Arg Lys Val Arg
1               5                   10

<210> SEQ ID NO 2
<211> LENGTH: 33
<212> TYPE: DNA
<213> ORGANISM: Artificial Sequence
<220> FEATURE:
<223> OTHER INFORMATION: DNA sequence encoding the active form of
      synthetic peptide LF11 based on human lactoferrin peptide

<400> SEQUENCE: 2
ttccaatggc aaaggaatat gagaaaagtg cgt                                 33

<210> SEQ ID NO 3
<211> LENGTH: 11
<212> TYPE: PRT
<213> ORGANISM: Artificial Sequence
<220> FEATURE:
<223> OTHER INFORMATION: Inactive form of synthetic peptide based on
      human lactoferrin peptide

<400> SEQUENCE: 3
```

Phe Gln Trp Gln Arg Asn Met Arg Arg Val Arg
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide STAT6 based on human
      statherin peptide

<400> SEQUENCE: 4

Asp Asp Asp Glu Glu Lys
1               5

<210> SEQ ID NO 5
<211> LENGTH: 18
<212> TYPE: DNA
<213> ORGANISM: Artificial Sequence
<220> FEATURE:
<223> OTHER INFORMATION: DNA sequence encoding synthetic peptide STAT6
      based on human statherin peptide

<400> SEQUENCE: 5
gatgatgatg aagagaaa                                                    18

<210> SEQ ID NO 6
<211> LENGTH: 18
<212> TYPE: DNA
<213> ORGANISM: Artificial Sequence
<220> FEATURE:
<223> OTHER INFORMATION: DNA sequence encoding synthetic peptide STAT6
      based on human statherin peptide

<400> SEQUENCE: 6
gatgatgatg aagaaaaa                                                    18

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide STAT15 based on human
      statherin peptide

<400> SEQUENCE: 7

Asp Asp Asp Glu Glu Lys Phe Leu Arg Arg Ile Gly Arg Phe Gly
1               5                   10                  15

<210> SEQ ID NO 8
<211> LENGTH: 45
<212> TYPE: DNA
<213> ORGANISM: Artificial Sequence
<220> FEATURE:
<223> OTHER INFORMATION: DNA sequence encoding synthetic peptide STAT15
      based on human statherin peptide

<400> SEQUENCE: 8
gatgatgatg aagagaaatt tttgcgtaga attggaagat tcggt                      45

<210> SEQ ID NO 9
<211> LENGTH: 17
<212> TYPE: PRT
<213> ORGANISM: Artificial Sequence
<220> FEATURE:
<223> OTHER INFORMATION: Synthetic fusion peptide STAT-LF6

<400> SEQUENCE: 9

```
Asp Asp Asp Glu Glu Lys Phe Gln Trp Gln Arg Asn Met Arg Lys Val
1               5                   10                  15
Arg

<210> SEQ ID NO 10
<211> LENGTH: 51
<212> TYPE: DNA
<213> ORGANISM: Artificial Sequence
<220> FEATURE:
<223> OTHER INFORMATION: DNA sequence encoding synthetic fusion peptide
      STAT-LF6

<400> SEQUENCE: 10
gatgatgatg aagagaaatt ccaatggcaa aggaatatga gaaaagtgcg t            51

<210> SEQ ID NO 11
<211> LENGTH: 51
<212> TYPE: DNA
<213> ORGANISM: Artificial Sequence
<220> FEATURE:
<223> OTHER INFORMATION: DNA sequence encoding synthetic fusion peptide
      STAT-LF6

<400> SEQUENCE: 11
gatgatgatg aagaaaaatt ccaatggcaa aggaatatga gaaaagtgcg t            51

<210> SEQ ID NO 12
<211> LENGTH: 26
<212> TYPE: PRT
<213> ORGANISM: Artificial Sequence
<220> FEATURE:
<223> OTHER INFORMATION: Synthetic fusion peptide STAT-LF15

<400> SEQUENCE: 12

Asp Asp Asp Glu Glu Lys Phe Leu Arg Arg Ile Gly Arg Phe Gly Phe
1               5                   10                  15

Gln Trp Gln Arg Asn Met Arg Lys Val Arg
            20                  25

<210> SEQ ID NO 13
<211> LENGTH: 45
<212> TYPE: DNA
<213> ORGANISM: Artificial Sequence
<220> FEATURE:
<223> OTHER INFORMATION: DNA sequence encoding synthetic fusion peptide
      STAT-LF15

<400> SEQUENCE: 13
gatgatgatg aagagaaatt tttgcgtaga attggaagat tcggt                   45
```

NATURAL POLYPEPTIDES FOR ORAL HEALTH CARE

CLAIM OF PRIORITY

This application claims priority to U.S. Provisional Application No. 60/880,753, filed Jan. 16, 2007, the disclosure of which is hereby incorporated by reference in its entirety.

BACKGROUND OF THE INVENTION

For many years researchers have attempted to develop chemotherapeutic agents that could be useful in combating infections in the oral cavity. As far back as the mid-1940's, with the introduction of antibiotics it became clear that although these potent agents had the potential to be effective, problems unique to the oral cavity interfered with their utility. As time went on bacterial plaque development in the oral cavity became better understood. With that better understanding it became clear that agents delivered to the oral cavity needed to adhere to oral tissues to resist removal by the flows of saliva and the forces of oral mastication. It became widely accepted that for antimicrobial agents to be effective in the oral cavity the agent (s) needed to be sustained in that environment over time. One experiment that illustrates this principle compared the efficacy of two prominent antimicrobial agents, tetracycline and penicillin. Penicillin was shown to be a more potent agent as compared to tetracycline when tested in-vitro. As such it was shown that Penicillin was effective against oral bacteria at a significantly lower concentration as compared to tetracycline when tested against bacteria grown in a broth media (1 ug/ml for Penicillin vs. 10-20 ug/ml for Tetracycline). Further, Penicillin is a bactericidal agent and thus promotes killing of bacteria, while tetracycline is bacteriostatic and thus slows bacterial growth and development. Nonetheless, in spite of these dramatic differences in potency, tetracycline proves to be a more effective anti-microbial agent when applied topically in the oral cavity. Thus when tetracycline was added to a salivary coated hydroxylapatite disk (SHA), a surrogate for the tooth/enamel surface, and then this tetracycline treated SHA tooth homologue was washed and then placed in a culture of bacteria it was seen that very few of these organisms were able to adhere to SHA. On the other hand when the SHA was treated in a similar manner with Penicillin there was no effect. Thus in spite of tetracycline's reduced potency when compared to Penicillin, tetracycline was superior in an assay that accounted for adherence and release of a drug from a salivary coated tooth analogue. Since the two most common dental diseases, caries and periodontal disease, result from oral bacteria that stick to the tooth surface, tests for antimicrobial efficacy in the oral cavity need to focus on ways to prevent or reduce bacteria from attaching to the tooth surfaces.

With that understanding, research in the late 1960's and early 1970's examined agents with the characteristic of substantivity, the ability of an agent to bind to and be released from a tooth-like surface. One of the first agents studied that possessed this characteristic was chlorhexidine, a bisbiguanide antimicrobial, that was shown both in vitro and in vivo to reduce bacterial plaque attachment to teeth. Agents known as Peridex® and Perioguard® were investigated and are currently commercially available oral mouth rinse agents that have been tested and shown to bind to the oral tissues. This property of substantivity combined with antimicrobial activity results in reduction in both gingivitis and caries levels when used in clinical studies. Since that time there have been many attempts to develop agents that work effectively in the oral cavity. Thus far clinical testing has demonstrated very few successes. One such success has utilized the agent, triclosan, the active ingredient in Colgate Total® toothpaste. This dentifrice has been tested sufficiently to receive the acceptance of federal agencies such as the ADA and the FDA. The commercially available dentifrice containing triclosan is produced by the Colgate Palmolive Company. Total toothpaste has been developed by taking a known antimicrobial, triclosan, a phenolic compound, that had been used in shampoos and deodorants, and linking it to an agent that allows it to bind to oral tissues. Three major industrial companies, Procter and Gamble, Unilever and Colgate Palmolive Company were all pursuing triclosan as an agent of possible effectiveness in the oral cavity at almost the same point in time. Each company had its own strategy that was designed to make the active agent, triclosan, bind to oral tissues so that it would be active against tooth binding oral microorganisms. To reiterate triclosan on its own did not bind to oral tissues and thus was ineffective in the oral cavity in spite of its potent antimicrobial properties The Colgate Palmolive Company mixed igicare or gantrex with triclosan to form a polymeric compound that when delivered to the oral cavity bound in such a way as to make the triclosan effective. This combination product, in addition to products containing chlorhexidine, and other agents containing phenolic compounds, are among the only effective agents developed in the last 40 years.

Caries is the single most common chronic childhood disease, five times more common than asthma. Over 70% of children over 17 years old have cavities. Over 108 million Americans lack dental health insurance so that treatment of this infection is lacking. *S. mutans* is considered one of the microbes most associated with dental decay. In studies of children with Localized Juvenile Periodontitis, now known as Localized Aggressive Periodontitis, one of the applicants found that many of these children have minimal decay. Further, these studies found that children with this form of periodontal disease have a variant in a salivary protein, lactoferrin (Lf). When this Lf variant, the lysine variant, was expressed in an insect vector and tested it was found to kill *Streptococcus mutans*. In contrast, another more common Lf variant, the arginine variant, present in healthy non-periodontal disease children had little to no effect on the survival of *S. mutans*.

Recently we have shown that a synthetic peptide with the lysine form of this lactoferrin protein kills *Streptococcus mutans*. Others have shown that lactoferrin peptides have antimicrobial activity, but no one to date has shown that the antibacterial activity derived from this peptide is useful against organisms in the oral cavity. We have also determined that the peptide will have limited usefulness in the oral cavity unless it is linked to something that will allow the peptide to bind to the tooth surface. Thus, we have developed a fusion peptide in which the active peptide is linked to a small salivary peptide, Statherin so that it can both retain its antimicrobial activity and also be retained on the tooth surface to reduce *S. mutans* binding to that surface.

Lactoferrin (Lf) is a multifunctional protein that is found in mammary secretion, tears and saliva and in the gastrointestinal tract. Its main function is to sequester iron from its surroundings to prevent oral microbes from attaining iron, a mineral necessary for survival. In addition, in its N-terminus, Lf has a region that has antimicrobial properties. This region is called the defensin region and it has been shown since 1980's that Lf can kill many types of bacteria including oral bacteria. It was also shown that within that N-terminus region, from amino acid position 11 to 31, at least two polymorphic forms exist. For the most part variation in this defensin region at amino acid position 29 can either contain arginine or lysine. As recently as 1998 it has been shown that these two variants in amino acid position 29 have different antimicrobial activities and that peptides designed with those forms could have antimicrobial activity. In fact our group in 2003 produced full length lactoferrin, secreted by insect cells. This insect cell secreted lactoferrin was produced with the two polymorphic forms (lysine and arginine) and was introduced by a baculovirus vector. The secreted protein had all the characteristic properties of human lactoferrin and we tested these two forms for activity against Gram+ and Gram− organisms. We found that the lysine form was more active against a range of Gram+ and Gram− organisms, and specifically more active against S. mutans, the reputed cause of dental caries. Since the lysine form of Lf was found more frequently in patients who had Localized Aggressive Periodontitis (LAP), a disease in which the children have less caries than their matched controls, we speculated that this lysine form of lactoferrin may provide an ecological advantage to these children that could explain the reduction in caries seen in these children. Further we then determined that pure lactoferrin would have limited usefulness in the oral cavity unless it was linked to something that would allow it to bind to the tooth surface. Statherin is a small salivary phosphoprotein found in saliva at concentrations of 200 ug/ml in stimulated saliva but at concentrations about 10-fold lower in non-stimulated saliva. Adsorption of salivary proteins onto enamel forms a pellicle coating of enamel to which bacteria in the mouth adhere forming the initial bacterial components of plaque. The initial salivary proteins that adsorb are the mucins, amylase, salivary IgA, lysozyme, cystatins, acidic proline rich proteins (PRPs) and agglutinins. Pellicle adsorption onto enamel or hydroxylapatite (HA) surfaces promotes the adherence of S. mutans. In contrast salivary proteins like statherin and histatins appear to have the opposite effect and thus inhibit S. mutans attachment (Gibbons and Hay 1989). Statherin is a tyrosine-rich phosphoprotein containing 43 amino acids (Hay and Moreno 1989). Statherin is most noted for its ability to reduce calculus formation by binding calcium (Hay and Moreno 1987). Recently, Shimotoyodeme et al (2006) have suggested that Statherin competes with high molecular weight salivary proteins to reduce S. mutans binding to the tooth surface. They further showed that a small peptide consisting of the first 6 amino acid also has this capacity. Until now, no evidence existed which would determine whether these amino acid residues could bind to another salivary protein or whether a fusion protein consisting of statherin and lactoferrin would still retain its ability to compete with other salivary proteins for a space on the tooth surface. Further, it was unknown whether a fusion peptide containing statherin would be retained on the enamel and whether this fusion peptide would retain its antimicrobial activity.

Described herein is a fusion peptide in which the antibacterial peptide (in the form of lactoferrin) is linked to a small salivary peptide (Statherin) that allows the antibacterial peptide to bind to the tooth surface and thus interfere with the ability of S. mutans to bind to the tooth surface.

SUMMARY OF THE INVENTION

The present invention is directed to the treatment of dental diseases caused by oral bacteria using Lactoferrin and Statherin fusion proteins, and compositions comprising the same.

In certain embodiments, the present invention is directed to a composition for inhibiting bacterial growth in the oral cavity comprising a fusion protein comprising a lysine form of a Lactoferrin polypeptide or a functionally equivalent peptide molecule thereof and a Statherin polypeptide or a functionally equivalent peptide molecule thereof.

In other embodiments, the present invention is directed to a fusion protein having SEQ ID NO. 10; SEQ ID NO. 11; or SEQ ID NO. 13, or a functionally equivalent peptide molecule thereof. In yet other embodiments, the present invention is directed to a composition comprising a fusion protein having SEQ ID NO. 10; SEQ ID NO. 11; or SEQ NO. 13, or a functionally equivalent peptide molecule thereof.

In further embodiments, the present invention is directed to a method for inhibiting bacteria in the oral cavity, the treatment or prevention of dental caries, the treatment or prevention of periodontal disease, the treatment or prevention of dental plaque or treating inflammation of the oral cavity associated with the presence of dental plaque by administering an effective amount of a composition comprising a fusion protein comprising a lysine form of a Lactoferrin polypeptide or a functionally equivalent peptide molecule thereof; and a Statherin polypeptide or a functionally equivalent peptide molecule thereof to a patient in need.

BRIEF DESCRIPTION OF THE DRAWINGS

FIG. 3: Diffusion assay showing that only one form of Lactoferrin possesses activity. In all panels the circle is a filter paper disk impregnated with different agents (PBS=phosphate buffered saline which is a control); LF "R"=the 11 mer of lactoferrin with arginine (R) in amino acid position 29; LF "K" the 11 mer of lactoferrin with lysine (K) in amino acid position 29. The disk containing a standard concentration of one of the agents is placed over a confluent culture of Streptococcus mutans. A clear zone around the disk shows that the agent has diffused into the agar medium and has inhibited the growth of the S. mutans culture and thus indicates that there is antibacterial activity and that the S. mutans can not grow in that area.

Panel Left: Disk impregnated with PBS=control showing no inhibition.

Panel Center: Disk impregnated with the arginine variant of Lactoferrin showing no clear zone and thus no inhibition of S. mutans.

Panel Right: Disk impregnated with the lysine variant of Lactoferrin showing a clear zone indicating that the agent has diffused into the agar and is inhibiting the growth of S. mutans.

FIG. 4: Diffusing assay showing that the most active fusion peptide is the LF and the Statherin 6 mer. Five panels are presented each evaluating the activity of the agents tested. In all panels the circle is a disk impregnated with different agents. The disk is placed over a confluent culture of Streptococcus mutans. A clear zone around the disk shows that there is antibacterial activity and that the S. mutans can not grow in that area.

Panel top left: Lactoferrin (11 mer) where the lysine is present. This formulation inhibits the growth of S. mutans seen as a clear zone around the disk.

Middle and top right panel are the two statherin peptides, a 6 mer and a 15 mer. Neither of these formulations has any antibacterial activity seen by the fact that no zone of inhibition is seen adjacent to the disk.

Panel bottom left: lactoferrin 11 mer noted as LF fused to the Statherin 6 mer. This fusion protein retains the activity of the Lactoferrin 11 mer.

Panel bottom right: Lactoferrin 11 mer noted as LF fused to Statherin 15 mer. This fusion protein has less activity than when LF is fused to the Stat 6 mer.

The two panels on the bottom show the level of interference when the LF is added to the two Statherins. The activity of the LF when the smaller Statherin peptide is fused to it is greater as compared to when the larger peptide is fused to the LF.

DETAILED DESCRIPTION OF THE INVENTION

The present invention relates to compositions for inhibiting bacterial colonization. For the purposes of this invention, the term "inhibiting" means the reducing or causing the death of existing bacteria, or impeding new bacterial growth. The invention is also for an oral therapeutic treatment which will inhibit bacterial colonization in the oral cavity thus reducing the quantity of dental plaque and caries. One embodiment of the invention is a substantially purified fusion protein consisting of Lactoferrin and Statherin (STAT-LF). Nucleic acid and amino acid sequences for STAT-LF are provided in FIG. 1. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition. In certain embodiments, the protein or polypeptide of the invention may be operatively linked to a second polypeptide sequence.

Functionally Equivalent Nucleic Acid Molecules

Figure 1:
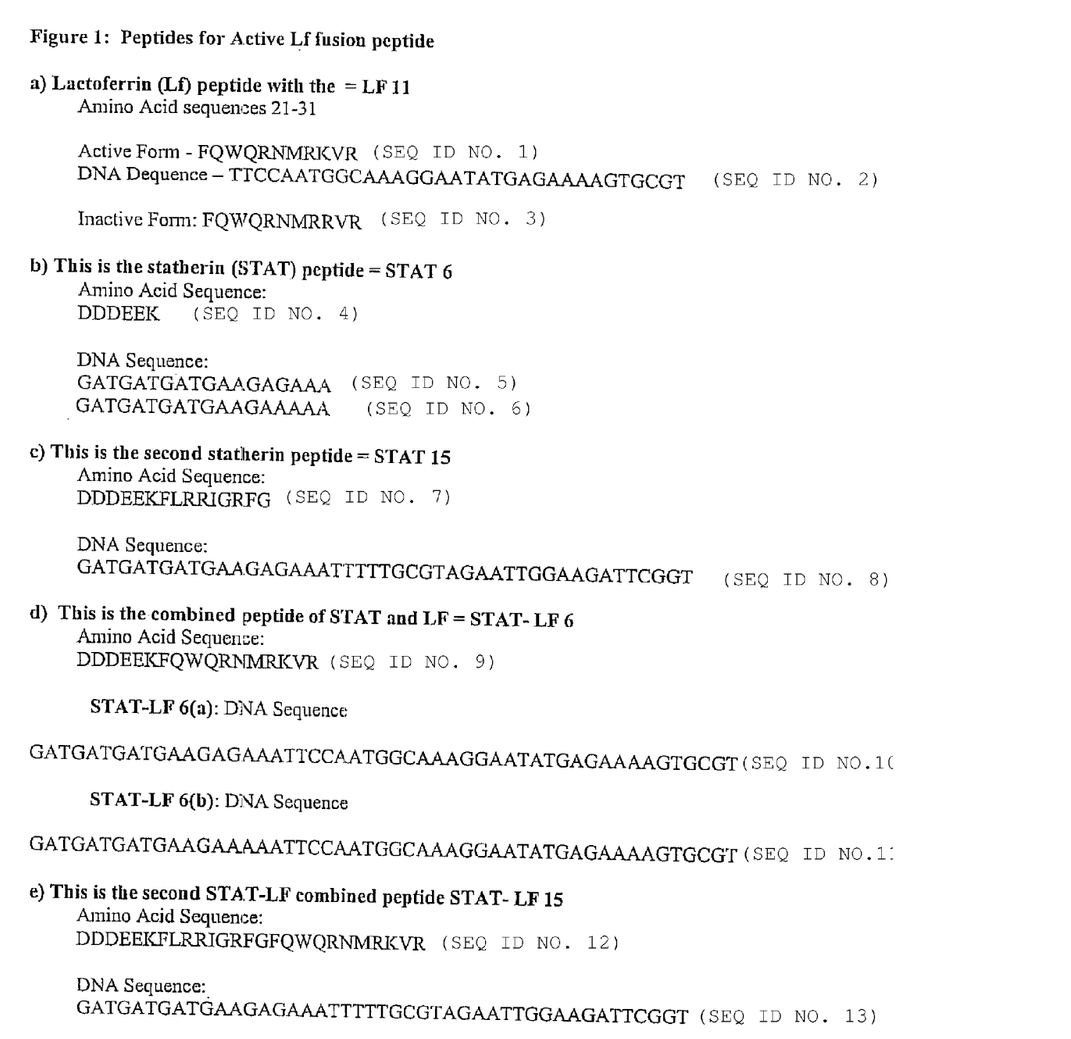
FIG. 1: Peptide Sequences of Lactoferrin, Statherin, and STAT-LF fusion proteins.
Figure 2:
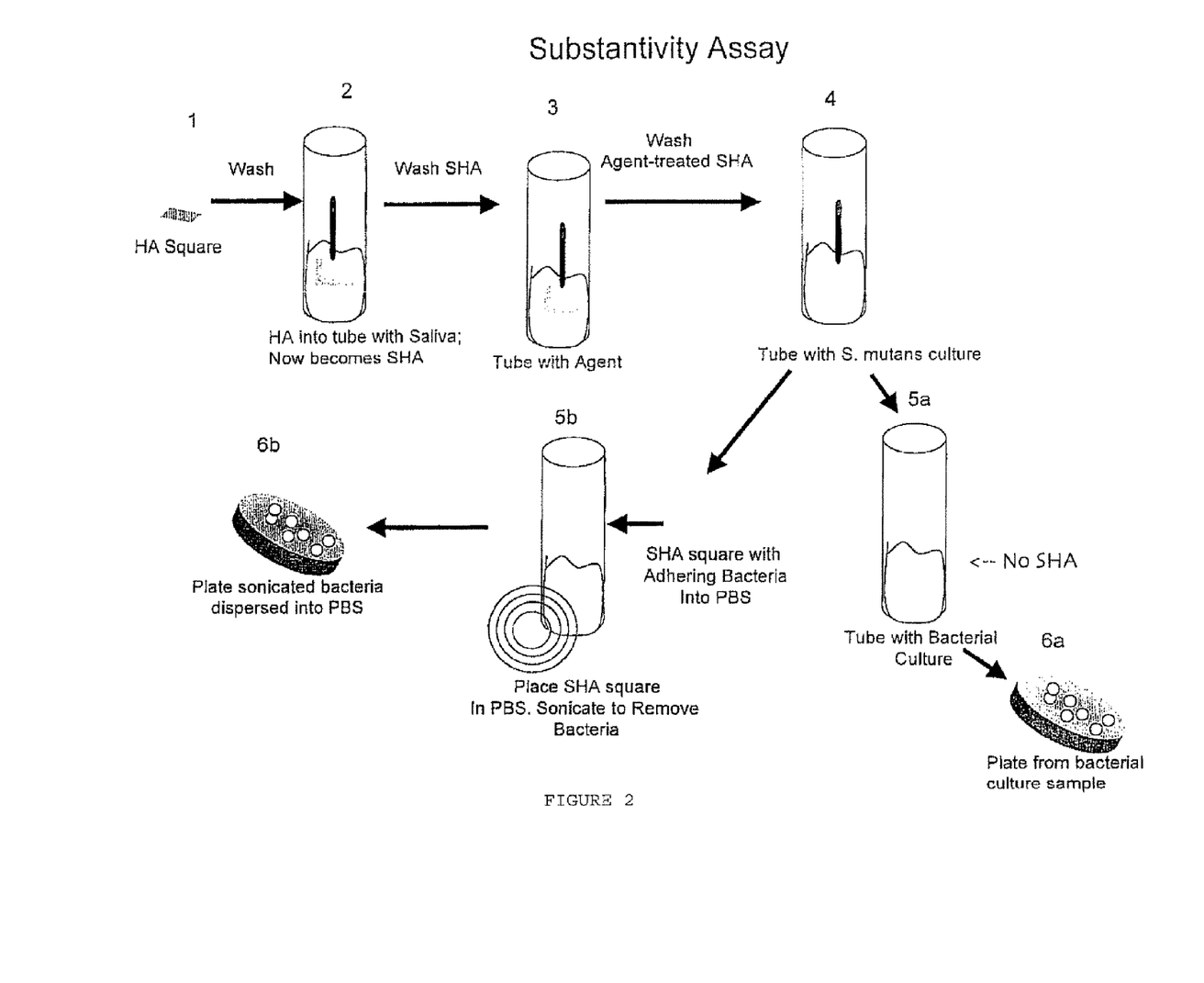
FIG. 2: Substantivity Assay illustrating the ability of the peptides to bind to the hydroxyapatite (HA) the tooth analogue.

Certain embodiments of the invention include nucleic acid molecules that are functional equivalents of all or part of the STAT-LF sequence. (A nucleic acid molecule may also be referred to as a DNA sequence or nucleotide sequence in this application. All these terms have the same meaning as nucleic acid molecule). Functionally equivalent nucleic acid molecules are DNA and RNA (such as genomic DNA, complementary DNA, synthetic DNA, and messenger RNA molecules) that encode peptides having the same or similar STAT-LF activity as the STAT-LF peptide as shown in FIG. 1. Functionally equivalent nucleic acid molecules can encode peptides that contain a region having sequence identity to a region of a STAT-LF peptide or more preferably to the entire STAT-LF peptide. Mutations described in this application preferably do not disrupt the reading frame of the coding sequence. Nucleic acid molecules functionally equivalent to the STAT-LF sequences can occur in a variety of forms as described below.

Nucleic acid molecules may encode conservative amino acid changes in STAT-LF peptide. Certain embodiments of the invention include functionally equivalent nucleic acid molecules that encode conservative amino acid changes within a STAT-LF amino acid sequence and produce silent amino acid changes in STAT-LF.

Nucleic acid molecules may encode non-conservative amino acid substitutions, additions or deletions in STAT-LF peptide. Some embodiments of the invention include functionally equivalent nucleic acid molecules that make non-conservative amino acid changes within the STAT-LF amino acid sequence (FIG. 1). Functionally equivalent nucleic acid molecules include DNA and RNA that encode peptides, peptides and proteins having non-conservative amino acid substitutions (preferably substitution of a chemically similar amino acid), additions, or deletions but which also retain the same or similar STAT-LF activity as the STAT-LF peptide. The DNA or RNA can encode fragments or variants of STAT-LF. The STAT-LF or STAT-LF-like activity of such fragments and variants is identified by assays as described below. Fragments and variants of STAT-LF encompassed by the present invention should preferably have at least about 40%, 60%, 80% or 95% sequence identity to the STAT-LF nucleic acids that encode the molecule, or a region of the sequence, such as the coding sequence or one of the conserved domains of the nucleic acid molecule.

Nucleic acid molecules functionally equivalent to the STAT-LF molecule in FIG. 1 will be apparent from the following description. For example, the sequence shown in [FIG. 1(d)] may have its length altered by natural or artificial mutations such as partial nucleotide insertion or deletion, so that when the entire length of the coding sequence within [FIG. 1(d)], is taken as 100%, the functional equivalent nucleic acid molecule preferably has a length of about 60-120% thereof, more preferably about 80-110% thereof. Fragments may be less than 60%.

Nucleic acid molecules containing partial (usually 80% or less, preferably 60% or less, more preferably 40% or less of the entire length) natural or artificial mutations so that some codons in these sequences code for different amino acids, but wherein the resulting peptide retains the same or similar STAT-LF activity. The mutated DNAs created in this manner should preferably encode a peptide having at least about 40%, preferably at least about 60%, at least about 80%, and more preferably at least about 90% or 95% sequence identity to the amino acid sequence of the STAT-LF peptide in [FIG. 1(d)].

Since the genetic code is degenerate, the nucleic acid sequence in [FIG. 1(d)] is not the only sequence which may code for a peptide having STAT-LF activity. This invention includes nucleic acid molecules that have the same essential genetic information as the nucleic acid molecule described in [FIG. 1(d)]. Nucleic acid molecules (including RNA) having one or more nucleic acid changes compared to the sequences described in this application and which result in production of a peptide shown in [FIG. 1(d)] are within the scope of various embodiments of the invention.

Other functional equivalent forms of STAT-LF-encoding nucleic acids can be isolated using conventional DNA-DNA or DNA-RNA hybridization techniques. Thus, certain embodiments of the present invention also include nucleic acid molecules that hybridize to one or more of the sequences in [FIG. 1(d)] or its complementary sequence, and that encode expression for peptides, peptides and proteins exhibiting the same or similar activity as that of the STAT-LF peptide produced by the DNA in [FIG. 1(d)] or its variants. Such nucleic acid molecules preferably hybridize to the sequence in [FIG. 1(d)] under moderate to high stringency conditions (see Sambrook et al. Molecular Cloning: A Laboratory Manual, Most Recent Edition, Cold Spring Harbor Laboratory Press, Cold Spring Harbor, N.Y.). High stringency washes have low salt (preferably about 0.2% SSC), and low stringency washes have high salt (preferably about 2% SSC). A temperature of about 37° C. or about 42° C. is considered low stringency, and a temperature of about 50-65° C. is high stringency. Some embodiments of the invention also include a method of identifying nucleic acid molecules encoding a STAT-LF activator peptide (preferably a mammalian peptide), including contacting a sample containing nucleic acid molecules including all or part of [FIG. 1(d)]

(preferably at least about 15 or 20 nucleotides of [FIG. 1(d)]) under moderate or high stringency hybridization conditions and identifying nucleic acid molecules which hybridize to the nucleic acid molecules including all or part of [FIG. 1(d)].). Similar methods are described in U.S. Pat. No. 5,851,788.

Certain embodiments of the present invention also include methods of using all or part of the nucleic acid molecules which hybridize to all or part of [FIG. 1(d)], for example as probes or in assays to identify antagonists or inhibitors of the peptides produced by the nucleic acid molecules (described below). Some embodiments of the present invention include methods of using nucleic acid molecules having sequence identity to the STAT-LF nucleic acid molecule (as described below) in similar methods.

Certain embodiments of the invention also include a nucleic acid molecule detection kit including, preferably in a suitable container means or attached to a surface, a nucleic acid molecule as disclosed herein encoding STAT-LF [FIG. 1(d)] or a peptide having STAT-LF activity and a detection reagent (such as a detectable label).

Pharmaceutical Compositions and Methods of Treatment

STAT-LF is also useful when combined with a carrier in a pharmaceutical composition. The compositions are useful when administered in methods of medical treatment or prophylaxis of a disease, disorder or abnormal physical state caused by *S. mutans*. Certain embodiments of the invention also include methods of medical treatment of a disease, disorder or abnormal physical state characterized by excessive *S. mutans*, for example by administering a pharmaceutical composition including a carrier and STAT-LF. Caries is one example of a disease, which can be treated or prevented by administering STAT-LF [FIG. 1(d)]. The compositions are also useful when administered in methods of medical treatment or prophylaxis of a disease, disorder or abnormal physical state caused by other dental plaque causing Gram+ or Gram− bacteria including but not limited to *Actinomyces* spp. and other *Streptococci* spp.

Pharmaceutical compositions can be administered to humans or animals by methods such as food, food additives, dentrifices, gels, toothpaste, mouthwash, dental floss, denture wash, denture adhesives, chewing gum, candies, biscuits, soft drinks or sports drinks in methods of medical treatment. STAT-LF may be coupled to lipids or carbohydrates. This increases their ability to adhere to teeth, either by prolonging the duration of the adhesion or by increasing its affinity, or both. They may also be coupled to polymers, for example in dental work (e.g. crowns, braces, fillings) or dental floss. Pharmaceutical compositions can be administered to humans or animals. Dosages to be administered depend on individual patient condition, indication of the drug, physical and chemical stability of the drug, toxicity of the desired effect and the chosen route of administration (Robert Rake), ed., Conn's Current Therapy (1995, W.B. Saunders Company, USA). Pharmaceutical compositions are used to treat diseases caused by dental plaque forming bacterial infections such as dental caries, periodontal disease and endocarditis. In a preferred embodiment, the pharmaceutical compositions are used to treat diseases caused by *Actinomyces* spp. and *Streptococci* spp. In a further preferred embodiment, the pharmaceutical compositions are used to treat diseases are used to treat Streptococci infections caused by but not limited to: *S. mutans, S. sobrinus, S. oralis, S. sanguis, S. mitis, S. gordonii, S. pneumoniae, S. pyogenes*, and *S. agalactiae*.

Nucleic acid molecules and STAT-LF [FIG. 1(d)] may be introduced into cells using in vivo delivery vehicles such as liposomes. They may also be introduced into these cells using physical techniques such as microinjection and electroporation or chemical methods such as coprecipitation or using liposomes. In some instances it will be desirable to employ liposomes targeted to the bacteria of interest.

In a preferred embodiment, pharmaceutical compositions according to the invention are prepared using one or more STAT-LF peptides capable of inhibiting biofilm formation in dental plaque associated bacteria.

Pharmaceutical compositions comprising STAT-LF peptides are particularly useful for methods of treatment or prevention (prophylaxis) of a disease, disorder or abnormal physical state caused by Streptococci infection. Such pharmaceutical compositions are especially useful for treating infections caused by one or more of one or more oral Streptococci bacteria such as *S. mutans, S. sobrinus, S. oralis, S. sanguis, S. mitis*, or *S. gordonii*. The pharmaceutical compositions are also useful for treating and preventing other types of Streptococci infections such as *S. pneumoniae, S. pyogenes*, and *S. agalactiae*.

Pharmaceutical compositions can be prepared by known methods for the preparation of pharmaceutically acceptable compositions which can be administered to patients, and such that an effective quantity of the nucleic acid molecule or peptide is combined in a mixture with a pharmaceutically acceptable vehicle. Suitable carriers are described, for example in Remington's Pharmaceutical Sciences (Remington's Pharmaceutical Sciences, Mack Publishing Company, Easton, Pa., USA). Carriers include saline and D5W (5% dextrose and water). Excipients include additives such as a buffer, solubilizer, surfactant, suspending agent, emulsifying agent, viscosity controlling agent, flavor, lactose filler, antioxidant, preservative or dye. There are preferred excipients for stabilizing peptides for parenteral and other administration. The excipients include serum albumin, glutamic or aspartic acid, phospholipids and fatty acids.

In other preferred embodiments, surfactants are included in the compositions to aid in the penetration of biofilm. The surfactants which may be used in the present invention generally include pharmaceutically acceptable anionic surfactants, cationic surfactants, amphoteric (amphipathic/amphophtlic) surfactants, and non-ionic surfactants. Suitable pharmaceutically acceptable anionic surfactants include, for example, monovalent alkyl carboxylates, acyl lactylates, alkyl ether carboxylates. N-acyl sarcosinates, polyvalent alkyl carbonates, N-acyl glutamates, fatty acid-polypeptide condensates, sulfuric acid esters, alkyl sulfates (including sodium lauryl sulfate (SLS)), ethoxylated alkyl sulfates, ester linked sulfonates (including docusate sodium or dioctyl sodium succinate (DSS)), alpha olefin sulfonates, and phosphated ethoxylated alcohols. Suitable pharmaceutically acceptable cationic surfactants include, for example, monoalkyl quaternary ammonium salts, dialkyl quaternary ammonium compounds, amidoamines, and aminimides. Suitable pharmaceutically acceptable amphoteric (amphipathic/amphophilic) surfactants, include, for example, N-substituted alkyl amides, N-alkyl betaines, sulfobetaines, and N-alkyl β-aminoproprionates.

In preferred embodiments, sodium laurel sulfate is used. En even more preferred embodiments, the composition comprises from about 0.1 to about 10%, from about 0.3 to about 5% or from about 0.5% to about 2% by volume of sodium lauryl sulfate. Alternatively, a substituted sequence on one of the lysine residues that embodies activities that convey activities like sodium lauryl sulfate may be inserted into the fusion peptide. For example, the side chain of Lys may be modified with undecanoic acid: this will introduce a long alkyl chain similar to the dodecyl moiety in SLS.

The side chain of Lys may also be modified with aminoundecanoic acid: this will introduce a long alkyl chain similar to the dodecyl moiety in SLS and a positive charge ($NH_2$) at the end.

The side chain Lys may also be modified, for example, with aminoundecanoic acid and couple aspartic acid at the end to introduce a zwitter ion at the end.

On this basis, pharmaceutical compositions could include an active compound or substance, such as a STAT-LF peptide, in association with one or more pharmaceutically acceptable vehicles or diluents, and contained in buffered solutions with a suitable pH and isoosmotic with the physiological fluids. A pharmaceutical carrier will depend on the intended route of administration. Methods of combining the active molecules with the vehicles or combining them with diluents are well known to those skilled in the art. Compositions may also contain additives such as antioxidants, buffers, bacteriostatis, bactericidal antibiotics and solutes which render the formulation isotonic in the intended recipient; and aqueous and non-aqueous sterile suspensions which may include suspending agents and thickening agents. The composition could include a targeting agent for the transport of the active compound to specified sites.

Pharmaceutical compositions according to the invention can be administered by any suitable route known in the art. In cases where the infection is localized, the pharmaceutical composition can be administered topically to infected area. In cases where the infection is systemic, the pharmaceutical composition may be administered orally, intravenously, or parenterally.

In some instances, it may be desirable to administer the pharmaceutical compositions according to the invention with a known antibacterial agent such as an antibiotic. In some instances, the pharmaceutical compositions which repress biofilm formation are also useful for rendering the bacterial cells more susceptible to antibiotics.

The term "antibiotic" as used herein refers to any compound known to one of ordinary skill in the art that will inhibit the growth of, or kill, bacteria. The term "antibiotic" includes, but is not limited to, beta-lactams (penicillins and cephalosporins), vancomycins, bacitracins, macrolides (erythromycins), lincosamides (clindomycin); chloramphenicols, tetracyclines, aminoglycosides (gentamicins), amphotericins, cefazolins, clindamycins, mupirocins, sulfonamides and trimethoprim, rifampicins, metronidazoles, quinolones, novobiocins, polymixins, gramicidins or any salts or variants thereof. The antibiotic used will depend on the type of bacterial infection.

A therapeutically effective dosage of the pharmaceutical compositions according to the invention will depend on the type and severity of the infection and whether the pharmaceutical composition comprises a further active ingredient such as an antibiotic. Generally, the therapeutically effective dose is the minimal amount sufficient for controlling biofilm formation or dental caries and which is not toxic to the human or animal treated. Methods for determining effective dosages and toxicity are known in the art.

According to another aspect of the present invention, there is provided a process of producing cells genetically modified to produce STAT-LF peptides which inhibit biofilm formation or dental caries. Another aspect comprises administering to a patient cells genetically modified to produce STAT-LF peptides which inhibit biofilm formation or dental caries.

A further aspect of the present invention provides the use in the preparation of a medicament for administration to a mammalian patient to improve oral health or to alleviate dental caries, of viable, transfected cells genetically modified to produce STAT-LF peptides which inhibits biofilm formation.

Antimicrobial Compositions

STAT-LF peptides described above for use in the preparation of pharmaceutical compositions can also be used to prepare antimicrobial compositions such as a liquid disinfecting solution. Such solutions may further comprise antimicrobials or antifungals such as alcohol, povidone-iodine solution and antibiotics as well as preservatives. These solutions can be used, for example, as disinfectants of the skin or surrounding area prior to insertion or implantation of a device such as a catheter, as catheter lock and/or flush solutions, and as antiseptic rinses for any medical device including, but not limited to catheter components such as needles, Leur-Lok connectors, needleless connectors and hubs as well as other implantable devices. These solutions can also be used to coat or disinfect surgical instruments including, but not limited to, clamps, forceps, scissors, skin hooks, tubing, needles, retractors, scalers, drills, chisels, rasps and saws.

Antimicrobial compositions for inhibiting biofilm formation may comprise any of the peptide, antisense and antibody STAT-LF peptides described above.

An antimicrobial composition may further comprise additional ingredients including but not limited to: a surfactant, an antiseptic and an antibiotic (see examples listed above).

Production of STAT-LF in Eukaryotic and Prokaryotic Cells

Nucleic acid molecules disclosed herein may be obtained from a cDNA library. Nucleotide molecules can also be obtained from other sources known in the art such as expressed sequence tag analysis or in vitro synthesis. The DNA described in this application (including variants that are functional equivalents) can be introduced into and expressed in a variety of eukaryotic and prokaryotic host cells. A recombinant nucleic acid molecule for the STAT-LF contains suitable operatively linked transcriptional or translational regulatory elements. Suitable regulatory elements are derived from a variety of sources, and they may be readily selected by one with ordinary skill in the art (Sambrook, J, Fritsch, E. E. & Maniatis, T. (Most Recent Edition). Molecular Cloning: A Laboratory Manual. Cold Spring Harbor Laboratory Press. New York: Ausubel et al. (Most Recent Edition). Current Protocols in Molecular Biology, John Wiley & Sons, Inc.). For example, if one were to upregulate the expression of the nucleic acid molecule, one could insert a sense sequence or silencing RNA and the appropriate promoter into the vector. Promoters can be inducible or constitutive, environmentally- or developmentally-regulated, or cell- or tissue-specific. Transcription is enhanced with promoters known in the art for expression. CMV and SV40 promoters are commonly used to express desired peptide in cells. Other promoters known in the art may also be used (many suitable promoters and vectors are described in the applications and patents referenced in this application).

If one were to downregulate the expression of the nucleic acid molecule, one could insert the antisense sequence and the appropriate promoter into the vehicle. A nucleic acid molecule may be either isolated from a native source (in sense or antisense orientations), synthesized, or it may be a mutated native or synthetic sequence or a combination of these.

Examples of regulatory elements include a transcriptional promoter and enhancer or RNA polymerase binding sequence, a ribosomal binding sequence, including a translation initiation signal. Additionally, depending on the vector employed, other genetic elements, such as selectable markers, may be incorporated into the recombinant molecule. Other regulatory regions that may be used include an enhancer domain and a termination region. Regulatory elements may bacterial, fungal, viral or avian in origin. Likewise regulatory elements may originate from animal, plant, yeast, insect or other sources, including synthetically produced elements and mutated elements.

In addition to using expression vectors described above, a peptide may be expressed by inserting a recombinant nucleic acid molecule in a known expression system derived from bacteria, viruses, yeast, mammals, insects, fungi or birds. A recombinant molecule may be introduced into cells by techniques such as *Agrobacterium tumefaciens*-mediated transformation, particle-bombardment-mediated transformation, direct uptake, microinjection, coprecipitation, transfection and electroporation depending on the cell type. Retroviral vectors, adenoviral vectors, Adeno Associated Virus (AAV) vectors, DNA virus vectors and liposomes may be used. Suitable constructs are inserted in an expression vector, which may also include markers for selection of transformed cells. A construct may be inserted at a site created by restriction enzymes.

In one embodiment of the invention, a cell is transfected with a nucleic acid molecule of the invention inserted in an expression vector to produce cells expressing a peptide encoded by the nucleic acid molecule.

Another embodiment of the invention relates to a method of transfecting a cell with a nucleic acid molecule disclosed herein, inserted in an expression vector to produce a cell expressing the STAT-LF peptide [FIG. 1] or other peptide of the invention. In accordance with certain embodiments of the invention a method is provided for expressing the disclosed peptides in a cell. A preferred process would include culturing a cell including a recombinant DNA vector including a nucleic acid molecule encoding STAT-LF [FIG. 1] (or another nucleic acid molecule of the invention) in a culture medium so that the peptide is expressed. The process preferably further includes recovering the peptide from the cells or culture medium.

Probes

Certain embodiments of the present invention include oligonucleotide probes made from the cloned STAT-LF peptide molecules described in this application or other nucleic acid molecules disclosed herein (see Materials and Methods section). Probes may be 15 to 20 peptides in length. A preferred probe is at least 15 peptides of STAT-LF in [FIG. 1]. Certain embodiments of the invention also include at least 15 consecutive nucleotides of [FIG. 1]. The probes are useful to identify nucleic acids encoding STAT-LF peptides as well as peptides functionally equivalent to STAT-LF. The oligonucleotide probes are capable of hybridizing to the sequence shown in [FIG. 1] under stringent hybridization conditions. A nucleic acid molecule encoding a peptide disclosed herein may be isolated from other organisms by screening a library under moderate to high stringency hybridization conditions with a labeled probe. The activity of the peptide encoded by the nucleic acid molecule is assessed by cloning and expression of the DNA. After the expression product is isolated, the peptide is assayed for STAT-LF activity as described in this application.

Functionally equivalent STAT-LF peptide molecules from other cells, or equivalent STAT-LF-encoding cDNAs or synthetic DNAs, can also be isolated by amplification using Polymerase Chain Reaction (PCR) methods. Oligonucleotide primers, such as degenerate primers, based on [FIG. 1] can be prepared and used with PCR and reverse transcriptase (E. S. Kawasaki (1990), In Innis et al., Eds., PCR Protocols, Academic Press, San Diego, Chapter 3, p. 21) to amplify functional equivalent DNAs from genomic or cDNA libraries of other organisms. Oligonucleotides can also be used as probes to screen cDNA libraries.

Functionally Equivalent Peptides, Peptides and Proteins

The present invention includes not only peptides encoded by the sequences disclosed herein, but also functionally equivalent peptides, peptides and proteins that exhibit the same or similar STAT-LF peptide activity as wells as mimetics (FIG. 1).

EXAMPLES

Methods

Two different experiments were performed to demonstrate the antimicrobial activity of the substances we tested. The first was a disk diffusion screening assay we developed in our laboratory. In that assay we grew an overnight culture of *S. mutans* in a broth consisting of trypticase soy and 20% sucrose added. Cells were grown overnight and then streaked to confluence on Mitis Salivarius Bacitracin (MSB) agar. In addition we took a 25 cm sterile filter paper disk and added 200 ul of either whole saliva, the saliva containing the lysine or the arginine variant of lactoferrin, allowed this saliva to dry onto the filter paper for 1 hour and then placed the filter paper containing the added protein over the center of the confluent culture of *S. mutans* on the MSB agar. This was then allowed to incubate at 37° C. for 24 hours after which we examined the plate for a zone of inhibition of *S. mutans* growth around the edge of the filter paper disk. This assay was used to screen for potential antimicrobial activity.

The second set of experiments consisted of growing a stock culture of *S. mutans* overnight in tryticase soy broth containing 20% sucrose (TSBS) which should yield approximately $1 \times 10^8$ cells per ml within a 24 hour period. We then thoroughly vortex this dense culture so that it was homogeneous and then took a 100 ul aliquot of this culture and put it into a new tube containing 9.8 ml of sterile TSBS to which we added 100 ul/ml of a 2 ug/ml dose of either; a) the lysine variant of Lf, b) the arginine variant of Lf, c) chlorhexidine [positive control], d) PBS [negative control]. This mixture was allowed to grow overnight. The next morning a 100 ul aliquot was removed placed on MSB agar, plated on this agar which is then grown overnight and examined the next day for colony forming units/ml. This set of experiments was used to compare and quantitate the antimicrobial activity of the Lf variants by means of standard MIC patterns of growth. These experiments were also done by mixing the bacterial cultures and the test agents for 1 to 2 hours and then plating overnight to determine the activity of the agent after a short period of contact time.

Figure 4:
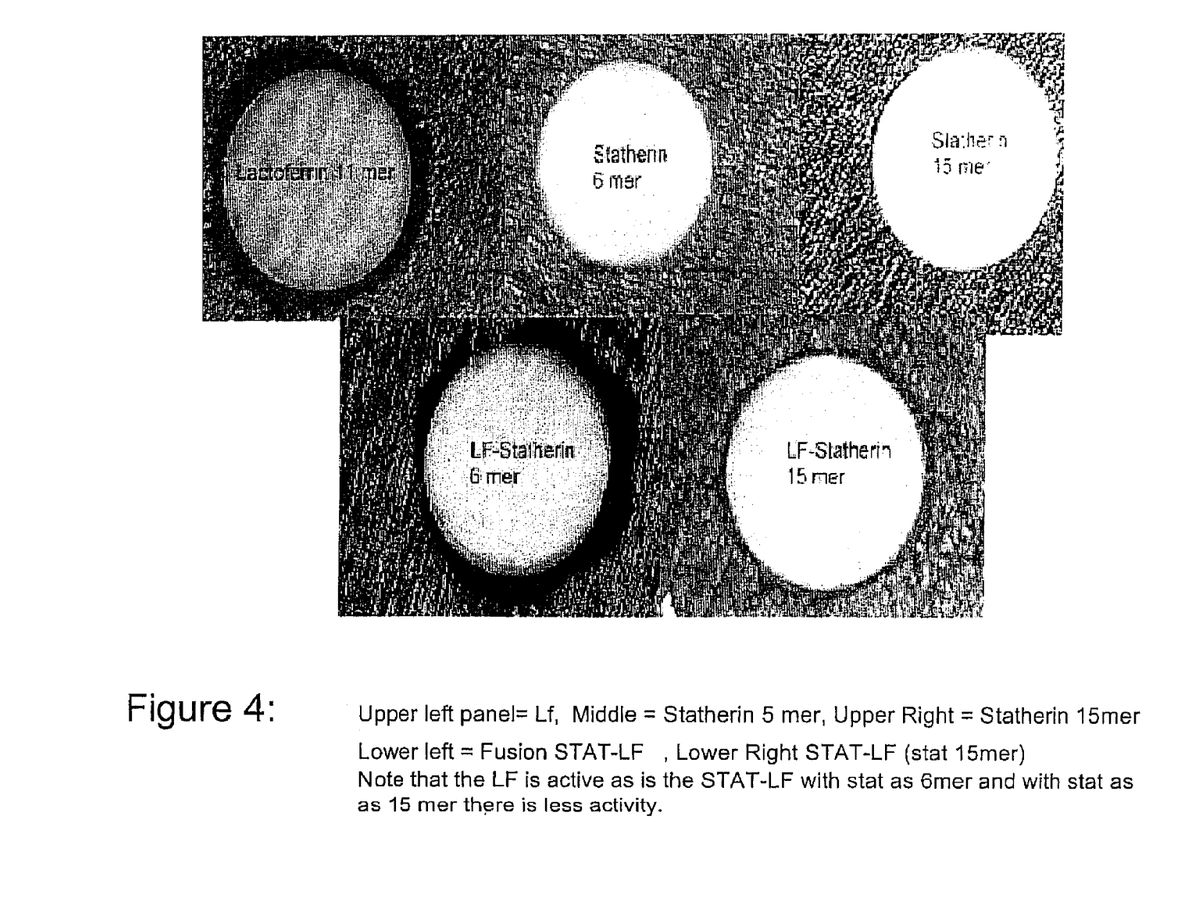
Figure 5:
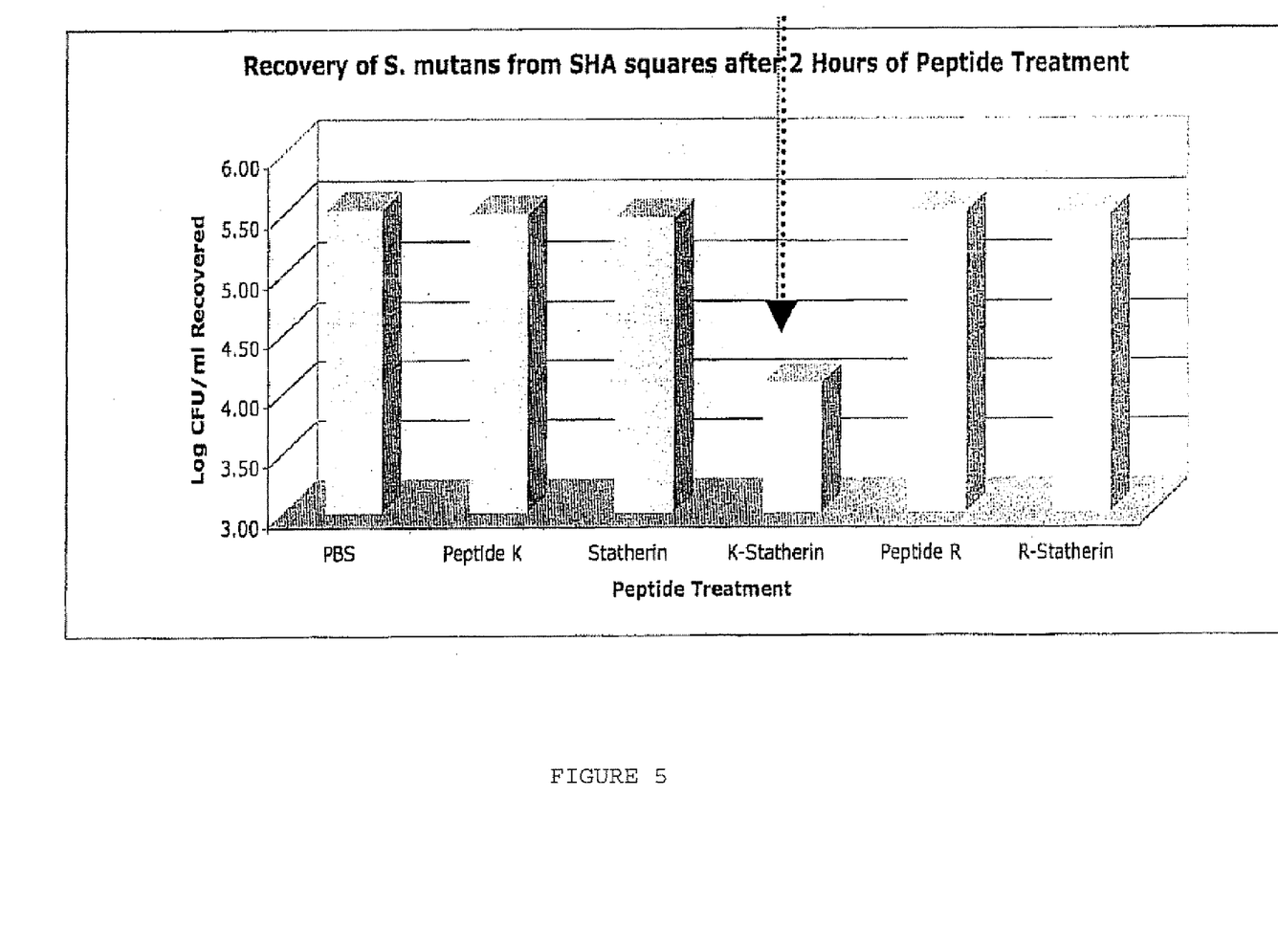
FIG. 5: Recovery of S. mutans from SHA squares after 2 hours of peptide treatment.

The third set of experiments utilized the Substantivity Assay, which demonstrates the ability of the peptides to bind to hydroxyapatite (HA) (FIG. 4). The results of the assay are provided in FIG. 5.

Method for Peptide Synthesis

The method used to synthesize peptides involves a stepwise addition of protected amino acids which were added to a solid resin particle by a covalent bond. The procedure uses Fmoc synthetic chemistry. The average cycle time for one amino acid addition took about 60 minutes. The added amino acids are protected. The protecting groups, used to protect the side chain functional groups are acid labile, while the N-terminal amino function of the amino acid is protected by the Fmoc group which is base vulnerable. The resin is in the form of 200-400 mesh porous beads which allows for the penetration of reagents into the gels mesh. The addition of the amino acids is done in a protected environment and then reagents and by-products are removed by filtration and recrystallization. The growing peptide chain is protected completely in the insoluble solid phase. The peptide formed is identical to samples prepared by the standard p-nitrophenyl ester procedure.

Figure 3:
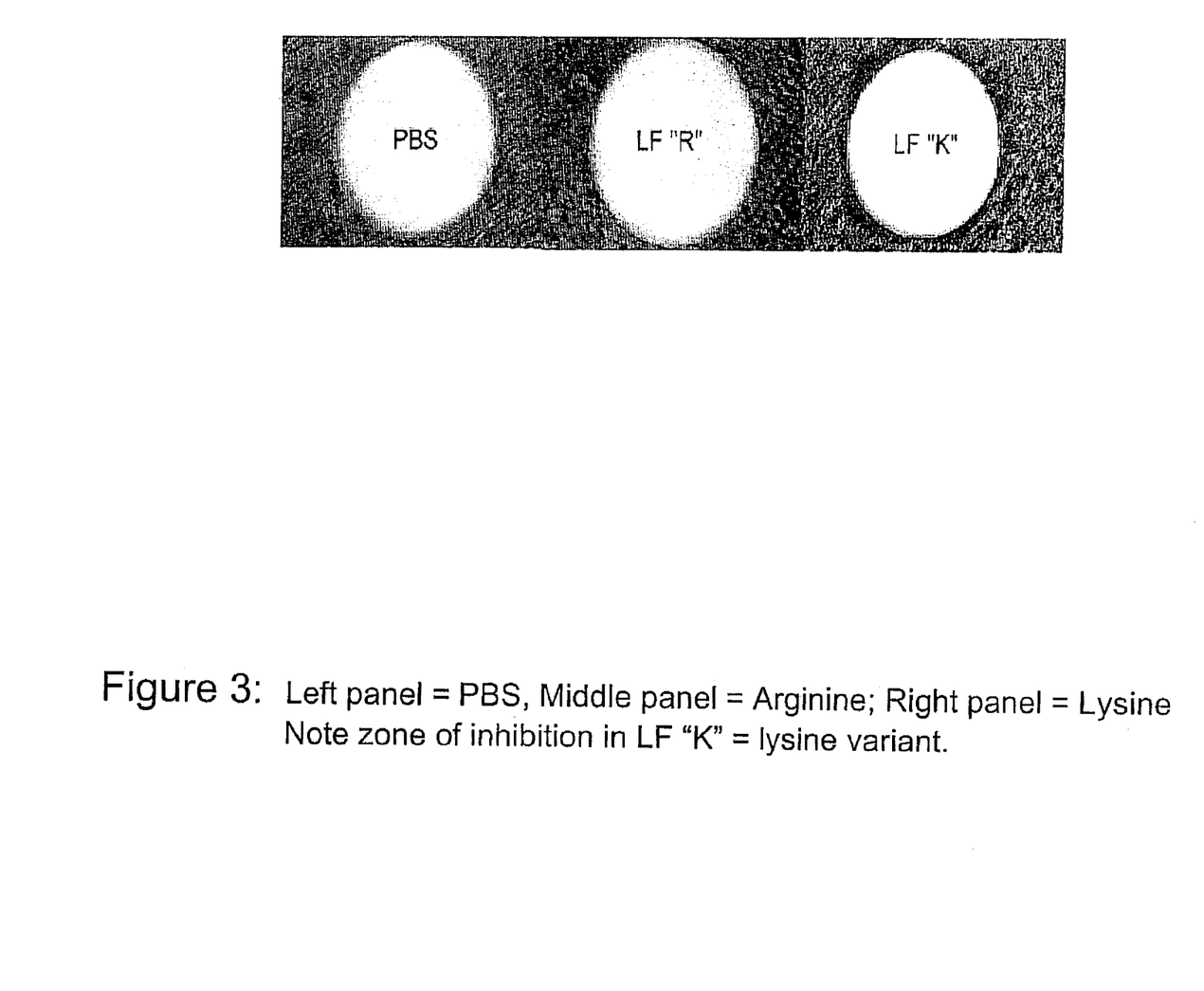

Results:

The disk diffusion assay allows for specific proteins to be added to a filter paper disk whereby the protein can then diffuse into the agar to determine antimicrobial activity. The following peptides were added to the disk; R=arginine form of Lf (FIG. 1(a)). K=lysine form of Lf (FIG. 1(a)). PBS=phosphate buffered saline which is used as the control solution and to which is added either the R form or K form of Lf. in FIG. 1 below we added R form, or the K form at a concentration of 1 ug/ml to 200 ul of PBS and then added that to the surface of a 25 cm filter paper strip and allowed the strip to dry for 1 hour. We then streaked a culture of S. mutans to confluence onto a plate of trypicase soy agar containing 20% sucrose and then placed the dried disk over the center of the plate. The cultures were allowed to grow in an incubator set at 37° C. and then evaluated either at 24 or 48 hours after inoculation. A zone of inhibition can be seen around disks K, where the lysine variant was suspended in PBS, and in disk K, where lysine was suspended in normal saliva (which had no antibacterial activity before the addition of K). No zone was seen on disk R/PBS or R/Saliva, where the arginine variant was substituted for the lysine variant (FIG. 3). The R and K Form of LF peptide was added at a concentration of about 15 ug/ml.

FIG. 4 shows that ST6 and ST15 do not have any antimicrobial activity. In the bottom row of FIG. 4, from left to right it can be seen that the LF 11 (FIG. 1) formulation inhibits the growth of S. mutans, seen as a clear zone around the disk. LF fused to the Statherin 6, this fusion protein retains the activity of the Lactoferrin 11 mer (FIG. 4). LF combined with ST 15, has less activity then STAT-LF 6.

What is claimed is:

1. A composition for inhibiting bacterial growth in the oral cavity comprising a fusion protein comprising:
   i. a lysine form of a Lactoferrin polypeptide and
   ii. a Statherin polypeptide.

2. The composition of claim 1, wherein the fusion protein is substantially purified.

3. The composition of claim 1, wherein the composition further comprises an ingredient selected from a pharmaceutically acceptable excipient, a surfactant or surfactant-like molecule, an antibacterial agent, an antimicrobial agent, an antifungal agent or combinations thereof.

4. The composition of claim 3, wherein the surfactant is sodium lauryl sulfate.

5. The composition of claim 1, wherein the fusion protein further comprises an additional a second polypeptide.

6. The composition of claim 1, wherein the fusion protein has SEQ ID NO: 10; SEQ ID NO: 11; or SEQ ID NO: 13.

7. A fusion protein having SEQ ID NO: 10, SEQ ID NO: 11, or SEQ ID NO: 13.

8. A method for inhibiting bacteria in the oral cavity comprising administering an effective amount of a composition comprising a fusion protein comprising:
   i. a lysine form of a Lactoferrin polypeptide and
   ii. a Statherin polypeptide to a patient in need thereof.

9. The method of claim 8, wherein the fusion protein is substantially purified.

10. The method of claim 8, wherein the composition further comprises an ingredient selected from a pharmaceutically acceptable excipient, a surfactant or surfactant-like molecule, an antibacterial agent, an antimicrobial agent, an antifungal agent or combinations thereof.

11. The method of claim 8, further comprising administering an effective amount of the surfactant or surfactant-like molecule to allow the composition to penetrate biofilm.

12. The method of any claim 8, wherein the fusion protein further comprises a second polypeptide.

13. A method for the treatment or prevention of an oral health condition comprising administering an effective amount of a composition comprising a fusion protein comprising:
   i. a lysine form of a Lactoferrin polypeptide and
   ii. a Statherin to a patient in need thereof.

14. The method of claim 13, wherein the oral health condition is selected from dental caries, periodontal disease, dental plaque and inflammation of the oral cavity.

15. The method of claim 13, wherein the fusion protein is substantially purified.

16. The method of claim 13, wherein the composition further comprises an ingredient selected from a pharmaceutically acceptable excipient, a surfactant or surfactant-like molecule, an antibacterial agent, an antimicrobial agent, an antifungal agent or combinations thereof.

17. The method of claim 13, further comprising administering an effective amount of a surfactant or surfactant-like molecule to allow the composition to penetrate biofilm.

18. The method of claim 13, wherein the fusion protein further comprises a second polypeptide.

* * * * *

UNITED STATES PATENT AND TRADEMARK OFFICE
CERTIFICATE OF CORRECTION

PATENT NO. : 8,129,329 B2
APPLICATION NO. : 12/523502
DATED : March 6, 2012
INVENTOR(S) : Daniel Fine et al.

It is certified that error appears in the above-identified patent and that said Letters Patent is hereby corrected as shown below:

In the Specification:

At column 4, line numbers 5-6, please delete "SEQ ID NO. 10; SEQ ID NO. 11; or SEQ ID NO. 13" and replace it with --SEQ ID NO. 9; or SEQ ID NO. 12-- therefor.

At column 4, line number 9, please delete "SEQ ID NO. 10; SEQ ID NO. 11; or SEQ ID NO. 13" and replace it with --SEQ ID NO. 9; or SEQ ID NO. 12-- therefor.

In the Claims:

At column 18, claim number 6, line number 53, please delete "SEQ ID NO. 10; SEQ ID NO. 11; or SEQ ID NO. 13" and replace it with --SEQ ID NO. 9; or SEQ ID NO. 12-- therefor.

At column 18, claim number 7, line numbers 54-55, please delete "SEQ ID NO. 10; SEQ ID NO. 11; or SEQ ID NO. 13" and replace it with --SEQ ID NO. 9; or SEQ ID NO. 12-- therefor.

Signed and Sealed this
Eleventh Day of June, 2013

Teresa Stanek Rea
*Acting Director of the United States Patent and Trademark Office*